United States Patent [19]
Keat et al.

[11] Patent Number: 5,019,668
[45] Date of Patent: May 28, 1991

[54] RECOVERY OF CAROTENOIDS

[75] Inventors: Ooi C. Keat, Butterworth; Choo Y. May; Augustine O. S. Hock, both of Kuala Lumpur, all of Malaysia

[73] Assignee: Palm Oil Research & Development Board, Selangor, Malaysia

[21] Appl. No.: 364,375

[22] Filed: Jun. 9, 1989

[30] Foreign Application Priority Data

Jun. 14, 1988 [AU] Australia ............................. 8768/88
Jun. 15, 1988 [AU] Australia ............................. 8770/88

[51] Int. Cl.$^5$ ............................. C07C 7/04; B01D 3/34
[52] U.S. Cl. ..................................... 585/864; 203/38; 426/540; 426/651
[58] Field of Search ................... 203/38, 28; 426/250, 426/540, 651; 585/800, 864

[56] References Cited

U.S. PATENT DOCUMENTS

| | | | |
|---|---|---|---|
| 2,383,581 | 5/1943 | Arrowsmith et al. | 260/410.7 R |
| 4,668,439 | 5/1987 | Biclenstein et al. | 260/410.9 R |
| 4,747,969 | 5/1988 | Rupicious et al. | 260/410.7 |
| 4,802,998 | 2/1989 | Mueller et al. | 252/49.3 |
| 4,849,132 | 7/1989 | Fujita et al. | 252/174.17 |

Primary Examiner—Patrick P. Garvin
Assistant Examiner—George R. Fourson
Attorney, Agent, or Firm—Willian Brinks Olds Hofer Gilson & Lione

[57] ABSTRACT

A process for the recovery of carotenes and the production of carotene concentrates from palm oil. Esterified palm oil containing carotenes, or other solutions containing carotenes, is mixed with an edible oil, part by part. The resulting mixture is subjected to a pressure of less than 7.999 N/m$^2$ and a temperature of less than 200° C., without incurring substantial decomposition of the carotenes during the process.

26 Claims, No Drawings

RECOVERY OF CAROTENOIDS

BACKGROUND OF THE INVENTION

This invention relates to the process of producing carotenoid concentrates and has particular but not exclusive application to the process of producing carotene concentrates from palm oil.

Carotenoids are the principal oil soluble yellow to orange red pigments found in plants and animals. Generally, there are two classes of carotenoids, that is the carotenes and xanthophylls. Carotenes are hydrocarbon carotenoids while xanthophylls are oxygenated carotenoids. Carotenoids are highly unsaturated compounds and are easily decomposed by heat, light and oxygen.

The more widely known carotenes are the alpha-, beta- and gamma-carotenes and lycopene. Some of the carotenes are precursors of vitamin A. Beta-carotene is a precusor of vitamin A and has also been shown to inhibit tumor progression, hence reduces cancer formation. As the carotenes are natural compounds with vitamin A property, they are widely used in commercial applications in the pharmaceutical and nutritional products.

The most important sources of carotenes are from vegetables, fruits and vegetable oil such as red palm oil. Among these sources, palm oil is the richest source of carotenes. The orange red color of palm oil is due to the presence of the carotenes. The concentration of carotenes in palm oil can range from 500 ppm to 3000 ppm, depending on the species of the palm fruit from which the oil is obtained. The commercial red palm oil contains about 500–700 ppm of carotenes of which alpha- and beta-carotene formed up to 90% of the total carotenes. So far commercial production of natural carotenes comes mainly from carrots, while commercial extraction of carotenes from palm oil is not very successful.

Some of the common techniques used in the recovery of carotenes from palm oil are saponification followed by extraction, adsorbent method, extraction by selective solvents, crystallization and molecular distillation of carotenes from the oil. In most of these techniques, large scale production of the carotenes from palm oil will be very expensive and involves too many steps in the process.

SUMMARY OF THE INVENTION

The present invention accordingly provides a simple process for the recovery of carotenes present in an oil or solution which contains carotenes and the production of carotene concentrates from palm oil, which comprises the steps of mixing esterified palm oil containing carotenes, or other solution containing carotenes, with an edible oil, to form a mixture; followed by vacuum distillation by subjecting the resulting mixture to a pressure of less than 0.060 Torr and an elevated temperature of less than 200° C., without incurring substantial decomposition of the carotenes during the process.

The temperature is preferably in the range 50° to 200° C., more preferably 70° to 190° C. The pressure is preferably in the range 0.002 to 0.060 Torr. The percentage of edible oil added to the esterified oil containing carotenes or the other solution containing carotenes is preferably in the range 0.1% to 50%, more preferably 1% to 10%, parts by weight of the mixture.

According to one preferred embodiment of the invention, the esterified oil containing carotenes or the other solution containing carotenes is mixed with 0.1% to 50% parts by weight of an edible oil and the resulting mixture is passed through a distillation apparatus, preferably at a temperature range of 50° to 200° C. and a pressure range 0.002 to 0.060 Torr.

DETAILED DESCRIPTION

The esterified oil containing carotenes or the other solution containing carotenes can be the alkyl esters such as the methyl esters, ethyl esters, isopropyl esters or butyl esters of the fatty acids of palm oil and its products, or any other food grade solvents that made up the solution. The edible oil used is preferably palm oil and its products, such as palm olein, palm stearin, neutralized palm oil, neutralized palm olein, or other vegetable oils. In this process, the alkyl esters of the fatty acids of palm oil or its products, or the other food grade solvents of the solution containing the carotenes, in the mixture are distilled off, while the carotenes are concentrated in the edible oil fraction. The carotene concentrate is dark red in color. The carotenes in the concentrates or edible oil is substantially stable during over a long period of time and have a concentration of at least 1000 ppm and above. The concentration of the carotenes can range from 1000 ppm to 30,000 ppm or higher depending on the concentration of the starting material or proportion of edible oil that is added to the esterified oil containing carotenes or solution containing carotenes.

Preferably, the mixture is heated to the required temperature and then allowed to pass through a distillation apparatus where the temperature of the mixture is maintained and the required pressure created. The distilled alkyl esters or food grade solvents are collected in a separate container from the carotene concentrate.

Preferably, the esterified oil or esterified palm oil containing the carotenes are prepared via esterification or transesterification of palm oil or oils containing carotenes. The oil used in the esterification or transesterification is preferably palm oil, palm olein, or palm stearin or any other vegetable oil containing carotenes. The alkyl esters produced by the esterification or transesterification process are preferably the methyl, ethyl, isopropyl or butyl esters of the fatty acids. The edible oil added to the esterified oil containing carotenes or solution containing carotenes is preferably palm oil and palm oil products such as palm olein and palm stearin, other vegetable oils such as peanut, soybean, corn, rapeseed, sunflower, olive, palm-kernel, coconut and fish oils, in each case, either crude, degummed and bleached, refined bleached and deodorized or refined.

The present invention will now be illustrated by the following examples.

EXAMPLE 1

200 parts by weight of crude palm oil having a concentration of carotene of 645 ppm and free fatty acids of less than 5% was transesterified with 79 to 120 parts by weight of methanol and 0.5 to 1.0 parts by weight of a base catalyst. After the transesterification reaction, the ester was separated from the glycerol, and washed with water until the washing was neutral. The ester was then dried using drying agents or vacuum. The dried ester was still orange red in color and had a carotene content of 700 ppm.

200 parts by weight of dried ester was then added with 20 parts by weight of refined and deodorized (RD)

red palm oil. The resulting mixture was then passed through a vacuum distillation column at a pressure of 0.020 to 0.025 Torr and a temperature of 90° C. The concentration of carotene in the concentrate obtained after the distillation was 6570 ppm.

The experiment was repeated using different temperatures for distillation and the results are shown in Table 1.

TABLE 1

| Temperature (°C.) | 110 | 130 | 150 | 170 |
|---|---|---|---|---|
| Carotene Concentrate (ppm) | 6650 | 6687 | 6754 | 6985 |

EXAMPLE 2

200 parts by weight of the dried ester as prepared in Example 1 was added with 10 parts by weight of refined and deodorized (RD) red palm oil. The resulting mixture was then passed through a vacuum molecular distillation column at a pressure of 0.020 to 0.025 Torr and a temperature of 90° C. The concentration of carotene in the concentrate obtained after the distillation was 9673 ppm.

The experiment was repeated using different temperatures for distillation and the results are shown in Table 2.

TABLE 2

| Temperature (°C.) | 110 | 130 | 150 | 170 |
|---|---|---|---|---|
| Carotene Concentrate (ppm) | 9754 | 9799 | 9861 | 9980 |

EXAMPLE 3

200 parts by weight of the dried ester as prepared in Example 1 was added with 5 parts by weight of refined and deodorized (RD) red palm oil. The resulting mixture was then passed through a vacuum molecular distillation column at a pressure of 0.020 to 0.025 Torr and a temperature of 90° C. The concentration of carotene in the concentrate obtained after the distillation was 18,762 ppm.

The experiment was repeated using different temperatures for distillation and the results are shown in Table 3.

TABLE 3

| Temperature (°C.) | 110 | 130 | 150 | 170 |
|---|---|---|---|---|
| Carotene Concentrate (ppm) | 18,798 | 18,861 | 18,890 | 18,994 |

EXAMPLE 4

200 parts by weight of crude palm oil having a concentration of carotene of 645 ppm and free fatty acids of less than 5% was transesterified with 79 to 135 parts by weight of ethanol and 0.5 to 1.0 parts by weight of a base catalyst. After the transesterification reaction, the ester was separated from the glycerol, and washed with water until the washing was neutral. The ester was then dried using drying agents or vacuum. The dried ester was still orange red in color and has a carotene content of 705 ppm.

200 parts by weight of dried ester was then added with 20 parts by weight of redefined and deodorized (RD) red palm oil. The resulting mixture was then passed through a vacuum molecular distillation column at a pressure of 0.020 to 0.25 Torr and a temperature of 90° C. The concentration of carotene in the concentrate obtained after the distillation was 6508 ppm.

The experiment was repeated using different temperatures for distillation and the results are shown in Table 4

TABLE 4

| Temperatue (°C.) | 110 | 130 | 150 | 170 |
|---|---|---|---|---|
| Carotene Concentrate (ppm) | 6597 | 6637 | 6761 | 6887 |

EXAMPLE 5

200 parts by weight of the dried ester as prepared in Example 4 was added with 10 parts by weight of refined and deodorized (RD) red palm oil. The resulting mixture was then passed through a vacuum molecular distillation column at a pressure of 0.020 to 0.25 Torr and a temperature of 90° C. The concentration of carotene in the concentrate obtained after the distillation was 9558 ppm.

The experiment was repeated using different temperatures for distillation and the results are shown in Table 5.

TABLE 5

| Temperature (°C.) | 110 | 130 | 150 | 170 |
|---|---|---|---|---|
| Carotene Concentrate (ppm) | 9617 | 9695 | 9782 | 9901 |

EXAMPLE 6

200 parts by weight of the dried ester as prepared in Example 4 was added with 5 parts by weight of refined and deodorized (RD) red palm oil. The resulting mixture was then passed through a vacuum molecular distillation column at a pressure of 0.020 to 0.25 Torr and a temperature of 90° C. The concentration of carotene in the concentrate obtained after the distillation was 18,409 ppm.

The experiment was repeated using different temperatures for distillation and the results are shown in Table 6.

TABLE 6

| Temperture (°C.) | 110 | 130 | 150 | 170 |
|---|---|---|---|---|
| Carotene Concentrate (ppm) | 18,515 | 18,590 | 18,695 | 18,741 |

EXAMPLE 7

200 parts by weight of the dried ester as prepared in Example 4 was added with 5 parts by weight of refined and deodorized (RD) red palm oil. The resulting mixture was then passed through a vacuum molecular distillation column at a pressure of 0.002 to 0.004 Torr and a temperature of 150° C. The concentration of carotene in the concentrate obtained after the distillation was 20,783 ppm.

EXAMPLE 8

200 parts by weight of the dried ester as prepared in Example 4 was added with 5 parts by weight of refined bleached and deodorized (RBD) palm olein. The resulting mixture was then passed through a vacuum molecular distillation column at a pressure of 0.020 to 0.025 Torr and a temperature of 130° C. The concentration of carotene of the concentrate obtained after the distillation was 18,571 ppm.

EXAMPLE 9

200 parts by weight of the dried ester as prepared in Example 4 was added with 5 parts by weight of neutralized, bleached and degummed (NBD) palm oil. The resulting mixture was then passed through a vacuum molecular distillation column at a pressure of 0.020 to 0.025 Torr and a temperature of 90° C. The concentration of carotene in the concentrate obtained after the distillation was 19,048 ppm.

EXAMPLE 10

200 parts by weight of the dried ester as prepared in Example 4 was added with 5 parts by weight of refined bleached and deodorized (RBD) palm oil. The resulting mixture was then passed through a vacuum molecular distillation column at a pressure of 0.020 to 0.025 Torr and a temperature of 130° C. The concentration of carotene in the concentrate obtained after the distillation was 18,650 ppm.

EXAMPLE 11

200 parts by weight of the dried ester as prepared in Example 4 was added with 5 parts by weight of refined and deodorized (RD) red palm olein. The resulting mixture was then passed through a vacuum molecular distillation column at a pressure of 0.020 to 0.025 Torr and a temperature of 130° C. The concentration of carotene in the concentrate obtained after the distillation was 19,708 ppm.

Those skilled in the art will appreciate that the invention described herein is susceptible to variations and modifications other than those specifically described. It is to be understood that the invention includes all such variations and modifications.

The invention also includes all of the steps, features, compositions and compounds referred to or indicated in this specification, individually or collectively, and any and all combinations of any two or more of said steps or features.

We claim:

1. A process for the recovery of carotenes present in a triglyceride oil or solution which contains carotenes, substantially without destroying the carotenes present in the oil or solution, which comprises the steps of
   (a) transesterification of the triglyceride oil or solution which contains carotenes with a monohydric alcohol to produce glycerol and a monohydric alcohol ester, followed by
   (b) vacuum distillation of the resultant transesterified oil or solution; characterized by
   (1) the addition of 0.1 to 50% by weight of edible oil to the transesterified oil or solution which contains carotenes to form a mixture, and
   (2) subjecting the resulting mixture to a pressure of less than 0.060 Torr and a temperature of less than 200° C.

2. A process as claimed in claim 1, wherein the oil used in the transesterification process is crude palm oil.

3. A process as claimed in claim 1, wherein the oil used in the transesterification process is crude palm olein.

4. A process as claimed in claim 1, wherein the oil used in the transesterification process is crude palm stearin.

5. A process as claimed in claim 1, wherein the oil used in the transesterification process is neutralized palm oil.

6. A process as claimed in claim 1, wherein the oil used in the transesterification process is neutralized palm olein.

7. A process as claimed in claim 1, wherein the transesterified oil containing carotenes contains the methyl esters of the fatty acids.

8. A process as claimed in claim 1, wherein the transesterified oil containing carotenes contains the ethyl esters of the fatty acids.

9. A process as claimed in claim 1, wherein the transesterified oil containing carotenes contains the isopropyl esters of the fatty acids.

10. A process as claimed in claim 1, wherein the solution containing carotenes contains a food grade solvent or mixture of food grade solvents.

11. A process as claimed in claim 1, wherein the edible oil added to the transesterified oil containing carotenes or solution containing carotenes is crude palm oil.

12. A process as claimed in claim 1, wherein the edible oil added to the transesterified oil containing carotenes or solution containing carotenes is refined and deodorized red palm oil.

13. A process as claimed in claim 1, wherein the edible oil added to the transesterified oil containing carotenes or solution containing carotenes is refined, bleached and deodorized palm oil.

14. A process as claimed in claim 1, wherein the edible oil added to the transesterified oil containing carotenes or solution containing carotenes is neutralized, bleached and degummed palm oil.

15. A process as claimed in claim 1, wherein the edible oil added to the transesterified oil containing carotenes or solution containing carotenes is crude palm olein.

16. A process as claimed in claim 1, wherein the edible oil added to the transesterified oil containing carotenes or solution containing carotenes is neutralized, bleached and degummed palm olein.

17. A process as claimed in claim 1, wherein the edible oil added to the transesterified oil containing carotenes or solution containing carotenes is refined, bleached and deodorized palm olein.

18. A process as claimed in claim 1, wherein the edible oil added to the transesterified oil containing carotenes or solution containing carotenes is refined and deodorized red palm olein.

19. A process as claimed in claim 1, wherein the edible oil added to the transesterified oil containing carotenes or solution containing carotenes is neutralized palm oil.

20. A process as claimed in claim 1, wherein the edible oil added to the transesterified oil containing carotenes or solution containing carotenes is neutralized palm olein.

21. A process as claimed in claim 1, wherein the edible oil added to the transesterified oil containing carotenes or solution containing carotenes is refined, bleached and deodorized palm stearin.

22. A process as claimed in claim 1, wherein the edible oil added to the transesterified oil containing carotenes or solution containing carotenes is either soybean oil, corn oil, rapeseed oil, sunflower oil, olive oil, peanut oil, palmkernel oil, coconut oil, fish oil or carrot oil, or mixture thereof.

23. A process as claimed in claim 1, wherein the amount of edible oil added to the transesterified oil containing carotenes or solution containing carotenes is in the range of 1% to 10% by weight of the resulting mixture.

24. A process as claimed in claim 1, wherein the process of distillation of the resulting mixture is carried out at a temperature range of 70° to 190° C.

25. A process as claimed in claim 1, wherein the process of distillation of the resulting mixture is carried out at a pressure range of 0.002 to 0.060 Torr.

26. A process as claimed in claim 1, wherein the oil used in the transesterification process is neutralized palm stearin.

* * * * *